United States Patent
Coster et al.

(10) Patent No.: US 8,512,535 B2
(45) Date of Patent: Aug. 20, 2013

(54) MEASUREMENT CELL

(75) Inventors: Hans Gerard Leonard Coster, Randwick (AU); Terry Calvin Chilcott, Sans Souci (AU)

(73) Assignee: Inphaze Pty Ltd, Mosman, NSW (AU)

( * ) Notice: Subject to any disclaimer, the term of this patent is extended or adjusted under 35 U.S.C. 154(b) by 559 days.

(21) Appl. No.: 12/675,469

(22) PCT Filed: Aug. 29, 2008

(86) PCT No.: PCT/AU2008/001261
§ 371 (c)(1),
(2), (4) Date: Sep. 2, 2010

(87) PCT Pub. No.: WO2009/026630
PCT Pub. Date: Mar. 5, 2009

(65) Prior Publication Data
US 2010/0320087 A1   Dec. 23, 2010

(30) Foreign Application Priority Data

Aug. 29, 2007  (AU) ................................ 2007904668

(51) Int. Cl.
*G01N 27/403* (2006.01)
(52) U.S. Cl.
USPC ........................................ 204/404; 324/447
(58) Field of Classification Search
USPC ........... 324/425–450; 702/22, 30–32, 35–38; 204/194, 400–401, 404, 434, 232
See application file for complete search history.

(56) References Cited

U.S. PATENT DOCUMENTS

| | | | |
|---|---|---|---|
| 5,131,999 A * | 7/1992 | Gunasingham | 204/403.02 |
| 5,373,734 A * | 12/1994 | Shih et al. | 73/150 R |
| 6,466,881 B1 | 10/2002 | Shih et al. | |
| 2004/0212370 A1 | 10/2004 | Cunningham et al. | |
| 2005/0274611 A1* | 12/2005 | Schlichting | 204/401 |
| 2009/0027070 A1* | 1/2009 | Gelling | 324/693 |

FOREIGN PATENT DOCUMENTS

EP   1600765 A1   11/2005

OTHER PUBLICATIONS

International Search Report and Written Opinion dated Oct. 30, 2008.

* cited by examiner

*Primary Examiner* — J. Christopher Ball
(74) *Attorney, Agent, or Firm* — Thomas Horstemeyer, LLP

(57) ABSTRACT

A measurement cell provides electrochemical characterization of a sample. The cell includes a container in which a sample is located, the container having walls and a base defining an interior region for containing a conductive media. A base electrode is located adjacent a base of the container, a counter electrode is spaced from the base electrode and a reference electrode is located between the base and counter electrodes. Samples that may be characterized include the conductive media, an element forming the base electrode or a surface of the base electrode, an element in contact with the conductive media, or any two or more of these. The reference electrode contacts the conductive media between the base electrode and the counter electrode such that electrical paths are is established through the sample between the base electrode and the counter electrode and between the base electrode and the reference electrode.

16 Claims, 7 Drawing Sheets

Section A-A

Section A-A

Section B-B

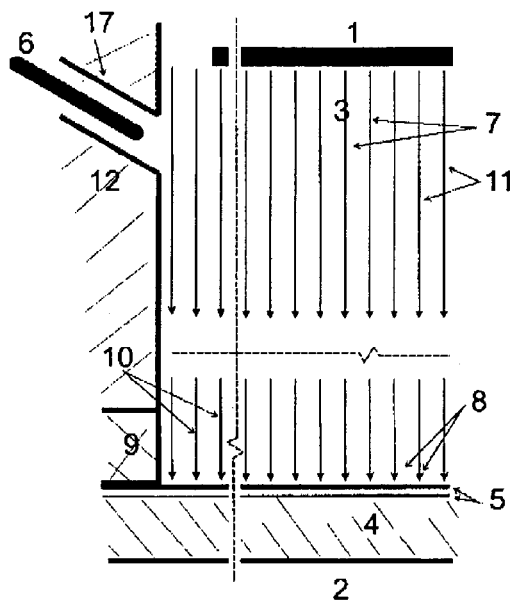 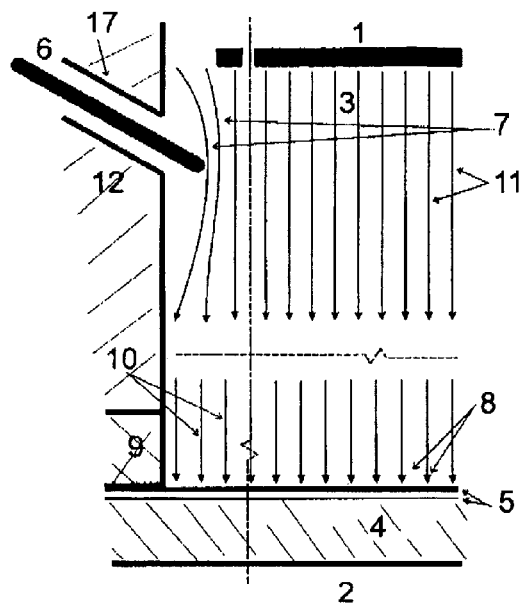
Figure 5  Figure 6
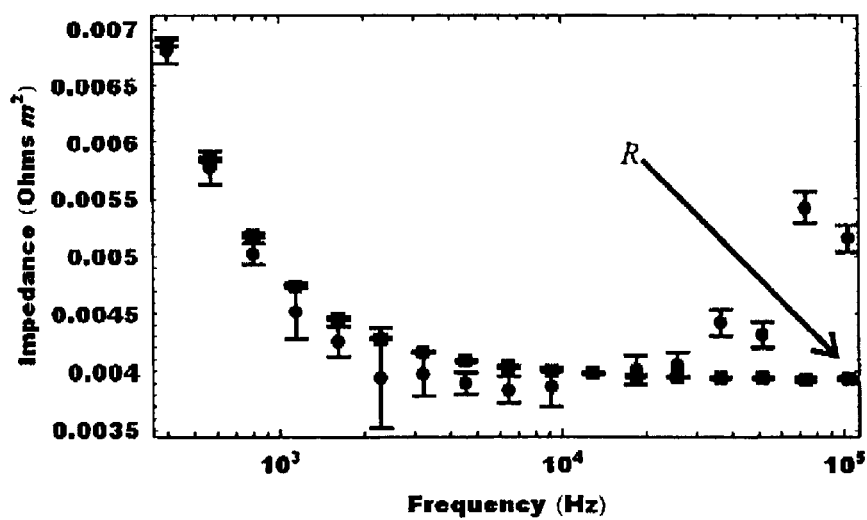
Figure 7

Section A-A

Section B-B

MEASUREMENT CELL

CROSS-REFERENCE TO RELATED APPLICATION

This application claims priority to PCT Application No. PCT/AU08/001,261, international filing date 29 Aug. 2008, which claims priority to Australian Application No. 2007904668, filed on 29 Aug. 2007.

INTRODUCTION

The present invention relates to the field of impedance spectroscopy and in particular the invention provides an improved measurement cell for electrochemical characterisation.

BACKGROUND

In the field of impedance spectroscopy, measurements may be affected by environmental elements external to the sample and often measurements are made on large samples to avoid the effects of such environmental elements. Many such effects can be balanced out but in the case of electrochemical characterisations, some distortions are the result of edge effects at the interface with the sample and its container and distortions caused by the physical presence of the electrode in the measurement chamber.

SUMMARY

According to a first aspect, the present invention provides a measurement cell fir electrochemical characterisation of a sample, comprising a sample container having walls defining an interior region in which the sample is contained, a first, base electrode located adjacent a base of the sample container, a second, counter electrode located spaced from the first, base electrode in the sample container, and a third, reference electrode and such that in use a first electrical path is established through the sample between the first, base electrode and the second, counter electrode and a second electrical path is established through the sample between the first, base electrode and the third, reference electrode.

According to a second aspect, the present invention provides a measurement cell for electrochemical characterisation of a sample, comprising a container in which a sample is located, the container having walls and a base defining an interior region for containing a conductive media, a first, base electrode located adjacent a base of the container, a second, counter electrode located spaced from the first, base electrode in the container, and a third, reference electrode located to contact the conductive media when in use, such that in use a first electrical path is established through the conductive media between the first, base electrode and the second, counter electrode and a second electrical path is established through the conductive media between the first, base electrode and the third, reference electrode.

The measurement cell may be configured to characterise a variety of samples including:

a) the conductive media; or b) a sample element located over and in electrical contact with the base electrode or forming a surface of the base electrode; and/or c) a sample element in contact with the conductive media, or d) a system combining two or more of a), b) and c).

The third electrode may be located in a passage through a wall of the container, the passage opening into the interior of the container between the first, base electrode and the second, counter electrode. In such cases the third, reference electrode may be located with its distal end within the passage such that the conductive media extends into the passage and contacts the third, reference electrode with no part of the third, reference electrode extending into the interior of the container.

In a particular embodiment of the measurement cell, the container comprises a planar container base, and a tubular containment element defining the walls an interior region in which the conductive media is contained, a seal being provided between the tubular containment element and the container base, the first, base electrode forming an inner surface of the container base or contacting the sample element which forms an inner surface of the container base and extending to meet an inner surface of the tubular containment element, or an extension of the inner surface, the second, counter electrode located spaced from the first, base electrode in the container, and the third, reference electrode located to contact the conductive media between the first, base electrode and the second, counter electrode.

According to a third aspect, the present invention provides a measurement cell for electrochemical characterisation of a sample, comprising a sample container having walls defining an interior region in which the sample is contained, a first, base electrode located adjacent a base of the sample container, a second, counter electrode located spaced from the first, base electrode in the sample container, and a third, reference electrode located in a passage through a wall of the sample container, the passage opening into the interior of the sample container between the first, base electrode and the second, counter electrode, the third, reference electrode being positionable with its distal end within the passage such that in use the sample extends into the passage to contact the third, reference electrode with no part of the third, reference electrode extending into the interior of the sample container, and in use a first electrical path is established through the sample between the first, base electrode and the second, counter electrode and a second electrical path is established through the sample between the first, base electrode and the third, reference electrode.

According to a fourth aspect, the present invention provides a measurement cell for electrochemical characterisation of a sample, comprising a container in which a sample is located, the container having walls and a base defining an interior region in which a conductive media is contained, a first, base electrode located adjacent a base of the container, a second, counter electrode located spaced from the first, base electrode in the container, and a third, reference electrode and wherein the third, reference electrode is located in a passage through a wall of the container, the passage opening into the interior of the container between the first, base electrode and the second, counter electrode, the third, reference electrode being positionable with its distal end within the passage such that in use the conductive media extends into the passage and contacts the third, reference electrode with no part of the third, reference electrode extending into the interior of the container, and in use a first electrical path is established through the conductive media between the first, base electrode and the second, counter electrode and a second electrical path is established through the conductive media between the first, base electrode and the third, reference electrode.

According to a fifth aspect, the present invention provides a measurement cell for electrochemical characterisation of a sample, comprising a sample container having a planar container base, and a tubular containment element defining the walls of an interior region in which the sample is contained, a seal being provided between the tubular containment element and the container base, a first, base electrode forming an inner surface of the container base and extending to meet an inner surface of the tubular containment element, or an extension of the inner surface, a second, counter electrode located spaced from the first, base electrode in the sample container, and a third, reference electrode positionable in use to contact the sample between the first, base electrode and the second, counter electrode, and in use a first electrical path is established through the sample between the first, base electrode and the second, counter electrode and a second electrical path is established through the sample between the first, base electrode and the third, reference electrode.

According to a sixth aspect, the present invention provides a measurement cell for electrochemical characterisation of a sample, comprising a container in which a sample is located, wherein the container has a planar container base, and a tubular containment element defining the walls of an interior region for containing a conductive media, a seal being provided between the tubular containment element and the container base, a first, base electrode forming an inner surface of the container base and the inner surface of the container base extending to meet an inner surface of the tubular containment element, or an extension of the inner surface, a second, counter electrode located spaced from the first, base electrode in the container, and a third, reference electrode, and wherein the third, reference electrode is positionable in use to contact the conductive media between the first, base electrode and the second, counter electrode, and in use a first electrical path is established through the conductive media between the first, base electrode and the second, counter electrode and a second electrical path is established through the conductive media between the first, base electrode and the third, reference electrode.

Preferably the intersection of the container base and the inner surface of the tubular containment element, or the extension of the inner surface, is essentially perpendicular. The container base and the inner surface of the tubular containment element are preferably substantially smooth.

The seal between the tubular containment element and the container base may comprise a sealing element located between the container base and the tubular containment element, in which case an inner surface of the seal will conform in shape with the inner surface of the tubular containment element and, in use, will form an extension of the inner surface of the tubular containment element. The inner surface of the tubular containment element is preferably circular in which case the sealing element will be annular.

The tubular containment element may be secured to the container base via a clamping device. The clamping device preferably includes a screw adjustment which provides adjustment of the pressure force clamping the elements together. In one embodiment the clamping device includes a single threaded screw element. Preferably also one or more spring elements are provided between the clamping device and the tubular containment element.

The clamping preferably comprises a clamp base and one or more threaded elements extending perpendicularly from the base. The threaded element or elements may comprise an outer housing and a threaded cap may engage the housing to bear down on the tubular containment element.

Alternatively threaded rods be secured to the base and extend through axially extending holes in the wall of the tubular containment element or they may extend adjacent the outside of the tubular containment element. Nuts may screw down on the threaded rods to bear on the tubular containment element to secure it in sealing engagement with the sealing element and the container base, by clamping the tubular containment element, the sealing element and the container base between the clamp base and the nuts. In one embodiment three threaded rods and respective nuts are provided equally spaced around the tubular containment element. The nuts are preferably "wing" nuts.

Spring elements may also be provided between threaded cap or the nuts and respective bearing points on the tubular containment element. The spring elements will preferably have a spring constant corresponding to a design compression force of the sealing element whereby partial compression of the spring element applies sufficient compression of the sealing element to seal the tubular containment element to the container base but not enough compression to significantly distort the inner surface of the sealing element such that it no longer represents an extension of the surface of the inner surface of the tubular containment element. If seals of different material are required for different samples (e.g. to avoid physical or chemical interaction of the seal material with the sample), different spring devices having different spring rates may be required, each matched to the compressibility of the particular seal material which in turn matches the physical and chemical characteristics of the sample or the base electrode structure.

BRIEF DESCRIPTION OF THE DRAWINGS

Embodiments of the measurement cell will now be described, by way of example with reference to the accompanying drawings in which:

FIG. 5 schematically illustrates an electrochemical characterisation apparatus featuring reference electrode 6 that is retracted in the recess and having a gasket 9 which is rectilinear in cross-section;

FIG. 6 schematically illustrates an Electrochemical characterisation apparatus featuring reference electrode 6 that is protruded out of the recess into the solution 3 and having a gasket 9 which is rectilinear in cross-section;

FIG. 7 graphically illustrates Electrical impedance measurements at high frequencies of a 100 mM KCl solution in contact with a rough gold wafer 4 and 5 using the Electrochemical characterisation apparatus shown in FIG. 5 (squares) and that shown in FIG. 6 (circles);

DETAILED DESCRIPTION OF AN EMBODIMENT

A characterisation apparatus combining a set of features that enable electrochemical characterisations of fragile samples and surfaces of small area to atomic resolutions is described herein. The apparatus may be used to characterise conductive fluids, solid materials and devices, membranes films and interfaces between such materials and devices. The examples discussed below are intended to explain the characterisation process using as an example a sample 5 located over a working electrode 4 and are not exhaustive of the types of samples that may be examined and cell configurations.

Figure 1:
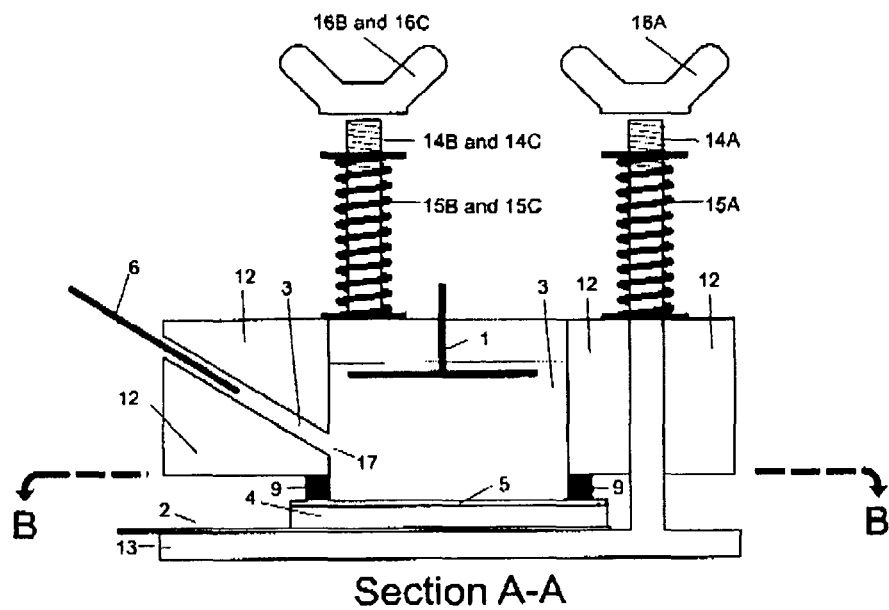
FIG. 1 schematically illustrates characterisation apparatus viewed through a vertical section A-A.
Figure 2:
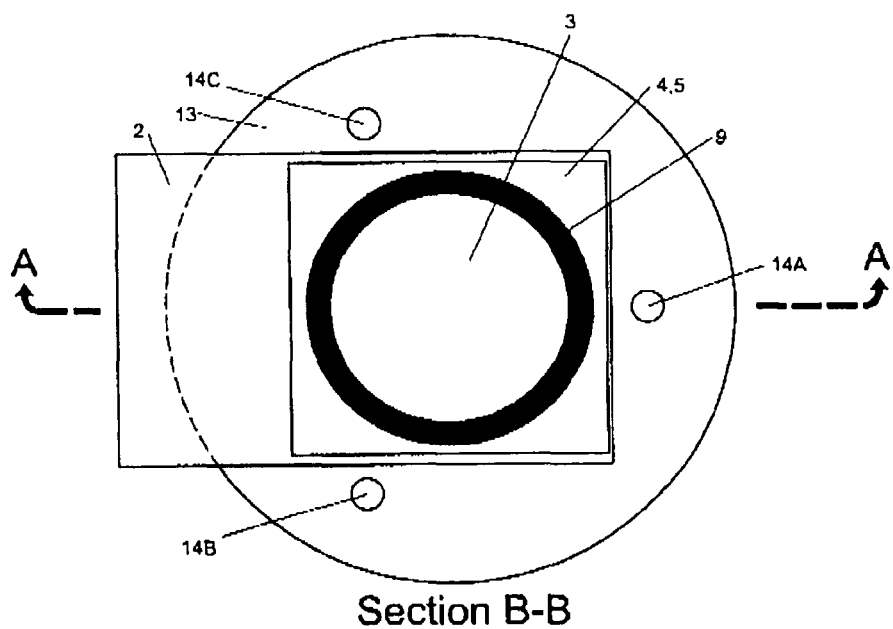
FIG. 2 schematically illustrates the apparatus of FIG. 1 viewed through a horizontal section B-B.

A schematic elevation and plan of an example of the apparatus are depicted in FIGS. 1 and 2. The principal structural components of the apparatus are a base 13 and a top 12 comprised of a chemically inert and electrically insulating material. The crucial set of features includes;
a recess 17 in the top of the apparatus 12 in which the reference electrode 6 resides, a gasket of rectilinear cross section 9 aligned with the inner vertical side of the top, and a set of three or more springs 15A, 15B and 15C mounted on posts 14A, 14 B and 14C that guide the assembly of the top 12, gasket 9, sample 4 and 5 and working electrode 2 with the base of the apparatus 13.

FIGS. 1 and 2 also depict a set of three or more bolts 16A, 16B and 16C that thread onto the guide posts and provide one method for accurately controlling the tensions in the springs and hence the magnitude and uniformity of the pressure on the surface 5 of the sample 4 during assemblies and characterisations.

Also depicted in FIG. 1 is a counter electrode 1 immersed in a fluid 3 that fills the chamber formed by the surface 5 of the sample, the vertical inner sides of the rectilinear gasket 9 and the inner vertical sides of the top 12 after assembly. The fluid 3 also permeates the recess 17 in the top where the reference electrode 6 is located. The means of physically supporting the counter electrode and perfusing the fluid are not shown.

An electrochemical characterisation proceeds by the stimulation of the sample 4 and surface 5 with a range of known currents via the working 2 and counter 1 electrodes and the measurement of responses via the reference 6 and working 2 electrodes.

The injection of a dc or ac stimulus is achieved via a working electrode 2 which supports the sample 4 and forms a low ohmic connection with it, and a counter electrode 1 immersed in a fluid 3 covering the surface layer 5 of the sample. The electric potential response of the system is measured via the working electrode 4 and a reference electrode 6 also immersed in the fluid but located closer to the sample than the counter electrode. A gasket 9 is used to seal a specific area of surface that makes contact with the fluid, called the 'active area' and through which the dc or ac stimulus flows.

Commonly the 'active area' is made as large as is practical in order to minimise effects on the density of the dc or ac at the circumference 11 where the fluid is contained by the gasket and densities are uncharacteristic of those at the sample surface 8. Further, the reference electrode 6 is, commonly, made as small as practical to minimise local effects 7 on the current density of the dc or ac that would be otherwise uniform 11. Additionally, the reference electrode is commonly located as close as practical to the surface of the sample in order to minimise the contribution of fluid between the reference and working electrodes to the total electrical response which, ideally, is principally the response of the sample.

Effectively the size, shape, location, and composition of the reference electrode may each adversely affect the accuracy of the characterisation of a sample 4 and its surface 5.

Figure 13:
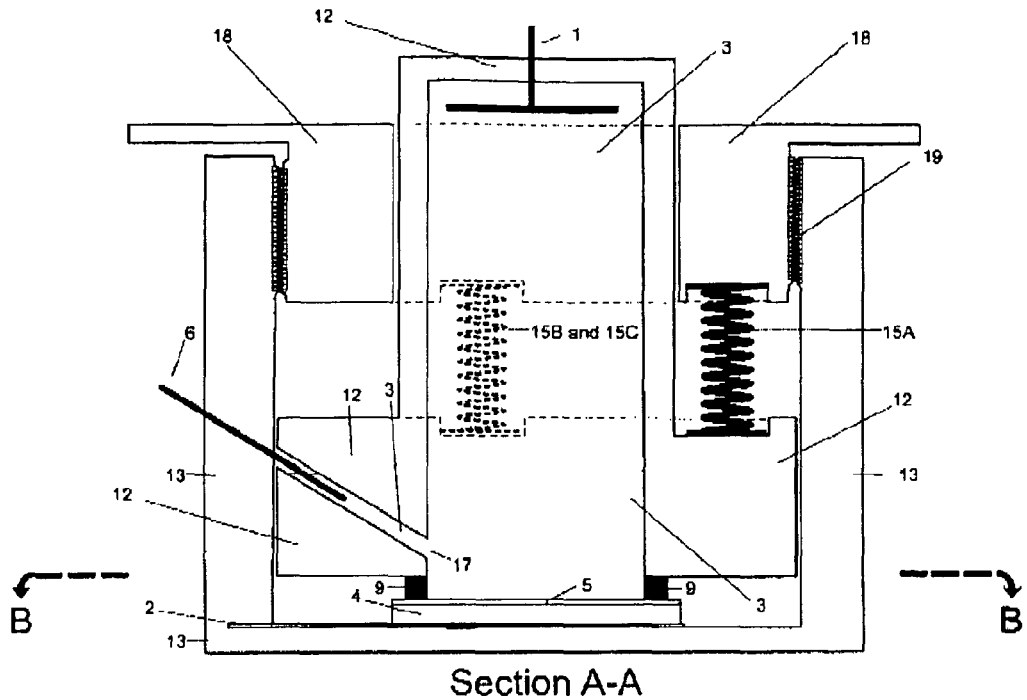
FIG. 13 schematically illustrates another embodiment of a characterisation apparatus viewed through a vertical section A-A.
Figure 14:
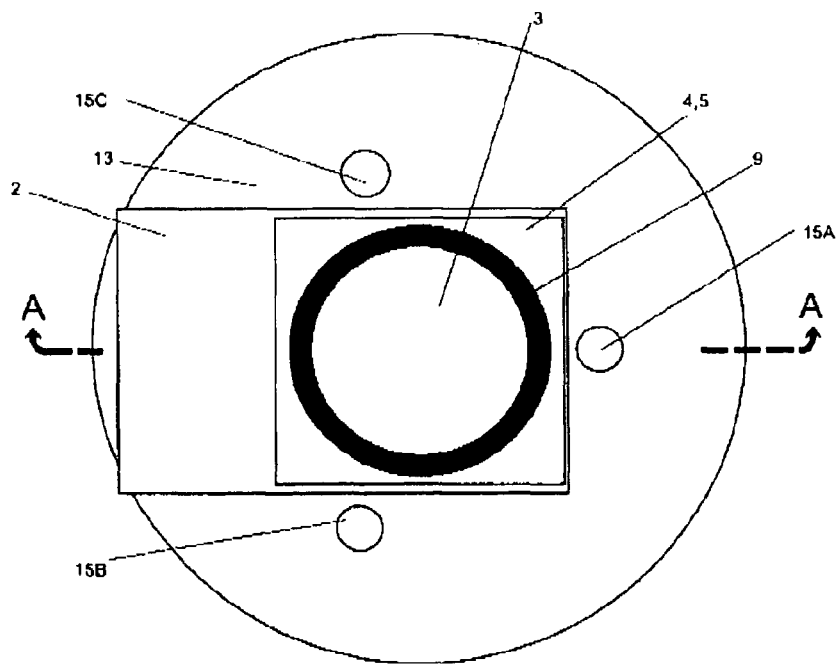
FIG. 14 schematically illustrates the apparatus of FIG. 13 viewed through a horizontal section B-B.

A schematic elevation and plan of a variation of the apparatus depicted in FIGS. 1 and 2 are shown in FIGS. 13 and 14, where FIG. 13 again schematically, illustrates this variation of the characterisation apparatus as viewed through a vertical section A-A and FIG. 14 illustrates this characterisation apparatus viewed through a horizontal section B-B. Parts indicated by item numbers in FIGS. 13 and 14 correspond to the parts with the same item numbers in FIGS. 1 and 2. The reference electrode 6 is retractable and is illustrated in the retracted position. The gasket 9 is of rectilinear cross-section with its inner surface located in line with the inner surface of the side wall 12 of the cell. The cylindrical chamber 12 is clamped onto the base electrode 4, 5 with the aid of a force transmitted, as before, through the springs 15A and two other springs 15B and 15C (hidden). However in this case a cap 18 engages the housing 13 via a threaded engagement 19 and the springs are simultaneously compressed by turning the cap 18. The threaded engagement 19 is designed to provide a smooth motion as the cap is screwed in or out. The retracted electrode 6 is located in a channel passage 17 which communicates with the cylindrical container 12.

The injection of the de or ac stimulus is achieved via a working electrode 4 which in the illustrated arrangement supports the sample 5 and forms a low ohmic connection with it (thereby acting as an extension of the working electrode 4), and a counter electrode 1 immersed in a fluid 3 covering the surface layer of the sample 5.

The retracted reference electrode 6 will avert disruption of the uniform current density 7 shown in FIG. 5 that would otherwise result if the protruded electrode were used (see FIG. 6). A gasket of rectilinear cross-section 9 similarly averts disruption of the uniform current density 11 shown in FIG. 5 at the edges of the active area of the sample. The material under test 5 is placed onto the base electrode 4 and the container 12 is clamped onto the test material and base electrode by the springs with sufficient pressure to seal the gasket 9 while not over stressing the sample 5.

Figure 3:
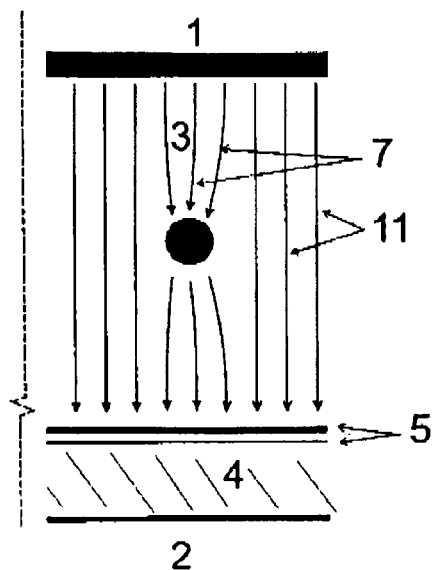
FIG. 3 schematically illustrates an electrochemical characterisation apparatus showing a type of non-uniform current density that can occur when the reference electrode 6 is more conducting than the fluid.

Effects of Size and Shape of the Reference Electrode on the Uniformity of the Current Density The size of the reference electrode will affect the local density of the current stimulus as illustrated in FIG. 3 for a cylindrically shaped reference electrode 6. It is assumed in FIG. 3 that the electrode is a better conductor than the fluid 3 whence the density of the dc or ac will be larger where current enters (and leaves) the electrode 7 than that density where it is spatially uniform 11. Conversely, FIG. 4 illustrates the effect of the same electrode when it is assumed to be less conducting than the fluid and the densities at these locations are less than where the density is spatially uniform 11.

Figure 4:
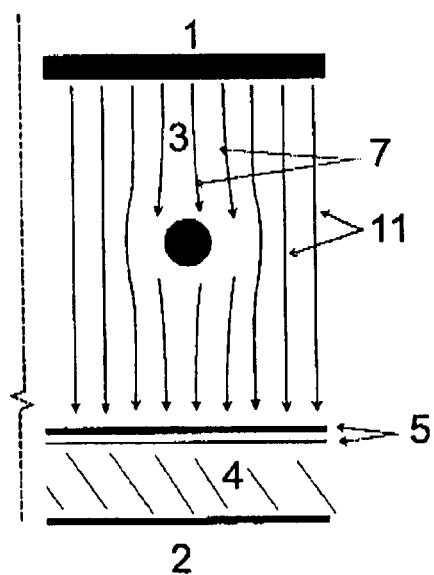
FIG. 4 schematically illustrates an electrochemical characterisation apparatus featuring a different type of non-uniform current density that can occur when the reference electrode is less conducting than the fluid.

For either scenario depicted in FIGS. 3 and 4, the effects of size on the density of the dc or ac will diminish with decreasing size and vanish when the electrode is ideally a point. Conversely these effects and any dependencies of these effects on the shape and electrical properties of the electrode will grow with increasing size.

The disruption of the spatially uniform current density by a reference electrode of any shape, size and composition will be associated with an electrical potential difference between the location of disruption 7 and a region of uniformity 11. So electrical potential measurements using a reference electrode unavoidably located in a region where the current density is disrupted 7 will be in error by this difference. The error will be uncharacteristic of the 'ideal' measurement associated with a stimulus of uniform density 11.

Dependence of Non-Uniform Current Densities Arising from the Properties of the Reference Electrode on Frequency For an alternating current (ac) the direction of the current alternates with time in a repetitive manner, i.e. at a particular frequency. Thus the lines 7, 11, 10, 8 representing the current in FIGS. 3 and 4 can also represent the ac in one-half of a cycle of the ac in which the arrows on these lines represent the direction of the ac. Lines with the arrows pointing in the opposite direction (not shown) can represent the ac for the other half-cycle. The frequency is defined as the rate at which the direction changes or the number of these cycles per unit of time.

The effect of the size and composition of the reference electrode on the local current density can become dependent on the frequency of the ac.

For example, a reference electrode comprised of an inert metal forms an ionic double layer when immersed in a fluid containing ions. The electrical properties of this layer are similar to that of an electrical insulator. At low frequencies the insulating properties of the double layer dominate diverting current around the reference electrode in a manner similar to that illustrated in FIG. 4. But at high frequencies the displacement current $$\left(\text{Displacement current} \equiv \varepsilon \frac{\partial \tilde{E}}{\partial t}\right)$$

dominates in the double layer 22 and the current flows into the reference electrode in a manner similar to that illustrated in FIG. 3.

So the error in the measured electrical potential difference in the location of disruption will be dependent on the frequency of the ac.

Effect of the Location of the Reference Electrode on the Uniformity of the Current Density The errors associated with the size and shape of the reference electrodes can be compounded further by the location of the reference electrode.

Whilst placing the reference electrode 6 as close as possible to the surface of the sample has the beneficial effect of minimising the contribution of the fluid to the total electrical response this can also introduce the non-uniform current density 3 associated with the reference electrode, to the surface of the sample. This non-uniformity 3 will be uncharacteristic of that produced by the surface alone 8.

Active Area

The accuracy of the characterisation is further dependent on measuring that area of sample subjected to the uniform current density, called the 'active area'. Nitrile annular gaskets or O-rings are commonly used to seal the 'active area', the area of which is readily calculated from the known and precise dimensions of the O-ring.

Effect of the Shape of the Gasket on the Uniformity of the Current Density

Figure 12:
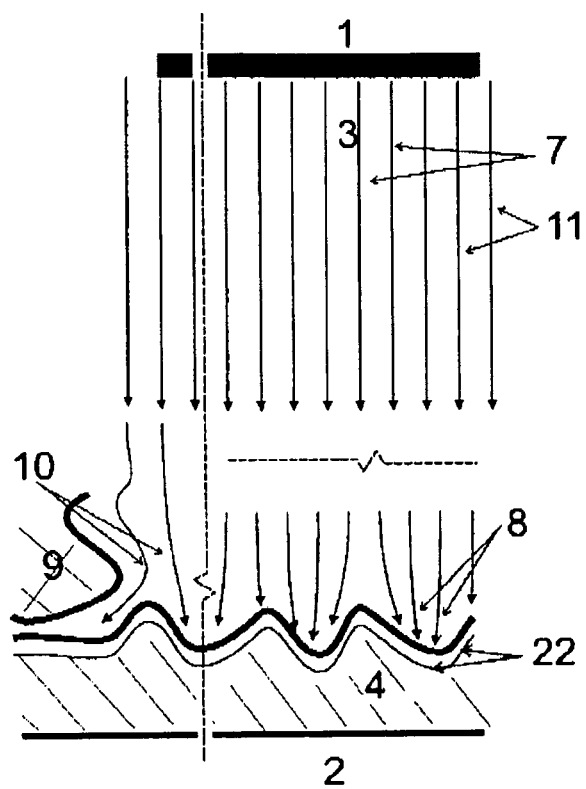
FIG. 12 schematically illustrates an electrochemical cell to illustrate the effect of surface roughness on the bottom electrode.

The disadvantage of using the O-ring or a gasket 9 of arbitrary profile shape is illustrated in FIG. 12. The profile shape of the gasket distorts the spatially uniform current density 11 in a similar manner to the reference electrode 3. In this instance, the non-uniform current density 10 produced by the gasket 9 will be uncharacteristic of the local current density 8 at the surface of the sample 5.

Effect of Frequency on Non-Uniform Current Densities Arising from the Properties of the Sample Surface and the Gasket Referring again to FIG. 12, the effect of the shape of the gasket on the local current density 11 can become dependent on the frequency of an alternating current (ac).

For example, a sample comprised of metal (illustrated in FIG. 12 as a rough surface on electrode 4 but which could for example be a metal sample located over the electrode) will form an ionic double layer 22 at the interface with a fluid containing ions. The dependency of the density of the current in the immediate vicinity of the surface on frequency will be similar to that described previously for that dependency for a reference electrode immersed in a fluid containing ions.

At low frequencies the insulating properties of the surface double layer 22 dominate and divert the ac away from the surface peaks creating a region of high density in the surface troughs of FIG. 12. Conversely at high frequencies the displacement current dominates in the double layer 22 and the regions of high density shift to surface peaks (not shown).

Similarly, the density is modified in the vicinity of the void between the surface and the gasket. However, in this instance, the insulating properties of the gasket will divert ac away from the gasket for both high and low frequencies. So at low frequencies the additional effect of the insulating properties of the double layer 22 will divert ac away from the void. Conversely, at high frequencies the displacement current in the double layer 22 will route the ac into the void.

The frequency dependent effects on the current density 10 occurring in the void will therefore be uncharacteristic of those effects on the density 8 occurring over the sample surface.

Impedance Characterisations of Rough Surfaces

Studies of the effects of non-uniform current densities have involved measurements of the electrical impedance of two identical metal electrodes of large surface area and varying roughness immersed in electrolytes of varying concentration. The large area minimises errors arising from edge effects. And as the two electrodes perform both current injecting and voltage sensing modes a reference electrode and its associated errors are eliminated from the measurement.

Impedance measurements were made by injecting an alternating current $i=i_o \sin(\omega t)$ of small amplitude $i_o$ and angular frequency $\omega$ into these electrodes. The same electrodes measured the voltage response $v=v_a \sin(\omega t+\omega)$ whence the impedance magnitude $(v_o/i_o)$ and phase $\Phi$ were determined. The measurements were repeated for a range of frequencies covering several decades.

The principal contributions to the measured impedance derived from the electrolyte and the interfacial layer (i.e. the double layer 22) that the metal forms with the electrolyte.

The impedance of the electrolyte is commonly modelled as a single resistance component R.

The impedance of the interfacial region is commonly represented by a constant-phase-angle (CPA) impedance element which disperses with frequency according to the expression;

$$Z_{CPA}(\omega) = \alpha(j\omega)^m = \alpha\omega^m e^{jm\pi/2} \text{ with } j \equiv \sqrt{-1} = e^{j\pi/2} \quad (1)$$

where $\alpha$ and m we constants. Note that the phase-angle is $m\pi/2$, which indeed is a constant in $\omega$. Many experiments have yielded values for m in the range;

$$-0.8 \leq m < -1 \tag{2}$$

with the flattest of the electrode surfaces yielding values for m approaching −1. The expected CPA for the flattest of surfaces, i.e. an atomically flat surface, is;

$$Z_{CPA}^{flat}(\omega) = \alpha(j\omega)^{-1} = \frac{1}{j\omega\left(\frac{1}{\alpha}\right)} \tag{3}$$

which is readily recognized as the impedance of a capacitor of capacitance $1/\alpha$. Equation (3) can be rearranged to define the capacitance of the CPA element for this special case so;

$$C_{CPA}^{flat} \equiv \frac{1}{j\omega Z_{CPA}^{flat}(\omega)} = \frac{1}{\alpha} \tag{4}$$

Generally the capacitance of the CPA element is given by;

$$C_{CPA}(\omega) \equiv \frac{1}{j\omega Z_{CPA}(\omega)} = C_{CPA}^{flat}(j\omega)^{-(m+1)} \tag{5}$$

The total impedance of the electrolyte in series with one of the interfacial regions is theoretically;

$$Z(\omega) = R + Z_{CPA}(\omega) = R + \frac{1}{j\omega C_{CPA}(\omega)} \tag{6}$$

At sufficiently high frequencies Equation (6) yields the resistance of the electrolyte, i.e.;

$$R \approx Z(\omega \to \infty) \tag{7}$$

And at sufficiently low frequencies;

$$C_{CPA}(\omega) \approx \frac{1}{j\omega Z(\omega \to 0)} \tag{8}$$

On this basis impedance measurements can distinguish between the properties of the electrolyte and those of metal-electrolyte interface by varying the frequency.

Effects of Non-Uniform Current Densities Produced by the Reference Electrode on Measurements of Impedance FIGS. 5 and 6 each schematically illustrate an electrochemical characterisation apparatus featuring reference electrode 6 that is either retracted in the recess as seen in FIG. 5 or protruded out of the recess into the solution 3 as seen in FIG. 6. Note that the gasket 9 is rectilinear in cross-section. In FIG. 7 Electrical impedance measurements at high frequencies of a 100 mM KCl solution in contact with a rough gold wafer 4 and 5 using the Electrochemical characterisation apparatus shown in FIG. 5 squares and that shown in FIG. 6 circles. The resistance R of the electrolyte is readily deduced from measurements using the recessed reference electrode.

FIG. 5 depicts a characterisation apparatus showing the preferred location for the reference electrode 6 and the preferred gasket of rectilinear cross-section located in line with the side wall 12 of the cell.

The retracted reference electrode see FIG. 5 will avert disruption of the uniform current density 11 that would result using the protruded electrode (see FIG. 4). A gasket of rectilinear cross-section similarly averts disruption of the uniform current density 11 at the edges of the active area of the sample.

FIG. 7 compares impedance measurements at high frequencies of a solution in contact with a gold sample 4 and 5 made with the reference electrode in either location. Measurements made with the reference electrode recessed (squares) approaches a value at high frequencies that is constant in frequency yielding precisely the resistance R of the electrolyte as per Equation (7). In contrast, measurements made with the reference electrode protruding into the solution and disrupting the otherwise uniform current density (circles) is markedly dependent on frequency, does not approach a constant value and only affords a possible range values for R.

Figure 8:
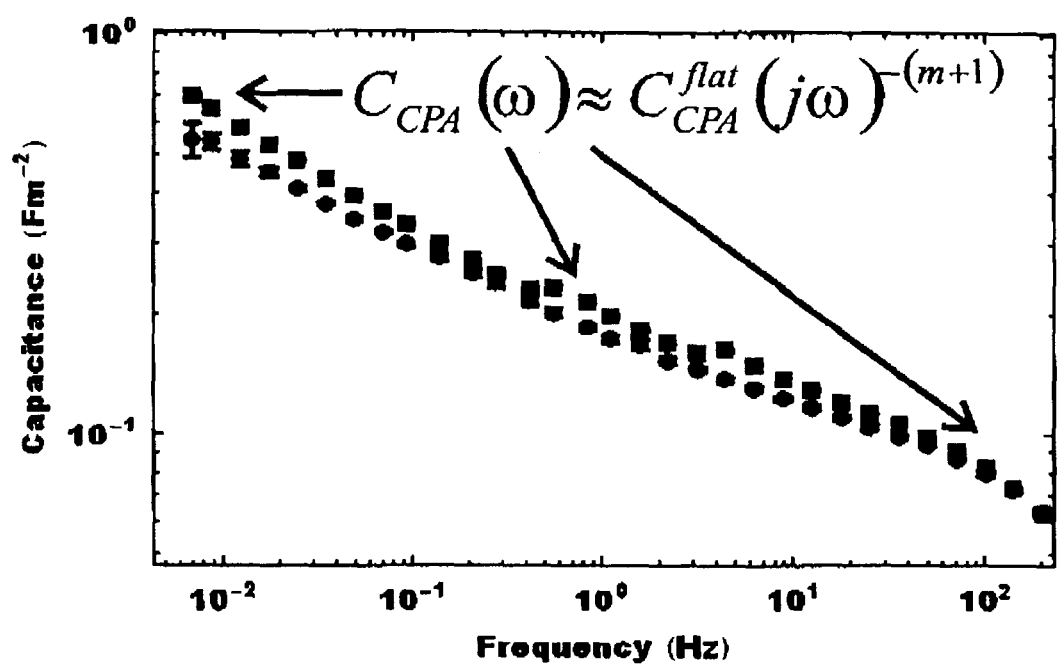
FIG. 8 graphically illustrates electrical capacitance measurements at low frequencies of a 100 mM KCl solution in contact with a rough gold wafer using a recessed (squares) and protruding (circles) reference electrode.

Electrical capacitance measurements at low frequencies are illustrated graphically in FIG. 8. For a 100 mM KCl solution in contact with a rough gold wafer using a recessed (squares) and protruding (circles) reference electrode. The dispersions of the capacitance with frequency using the electrode located in either location generally follow the CPA relationship given by Equation (5), in which $m \approx -0.8$.

Whilst the dispersions of the capacitance with frequency generally comply with the CPA behaviour over four decades of frequency, a direct comparison at each frequency reveals the capacitance measured using the reference electrode protruding into the electrolyte 3 underestimated that measured with this electrode recessed by a factor of $\approx 25\%$.

The measurements illustrated in FIG. 7 demonstrate that those made with the recessed reference electrode, unlike those made with the reference electrode protruding into the fluid, yield a definitive value for the electrolyte resistance that is constant in frequency and consistent with theoretical expectations from the literature. Those measurements illustrated in FIG. 8 further demonstrate the manifestation of errors in the characterisation of the sample surface using the protruding electrode.

Figures 9, 10:
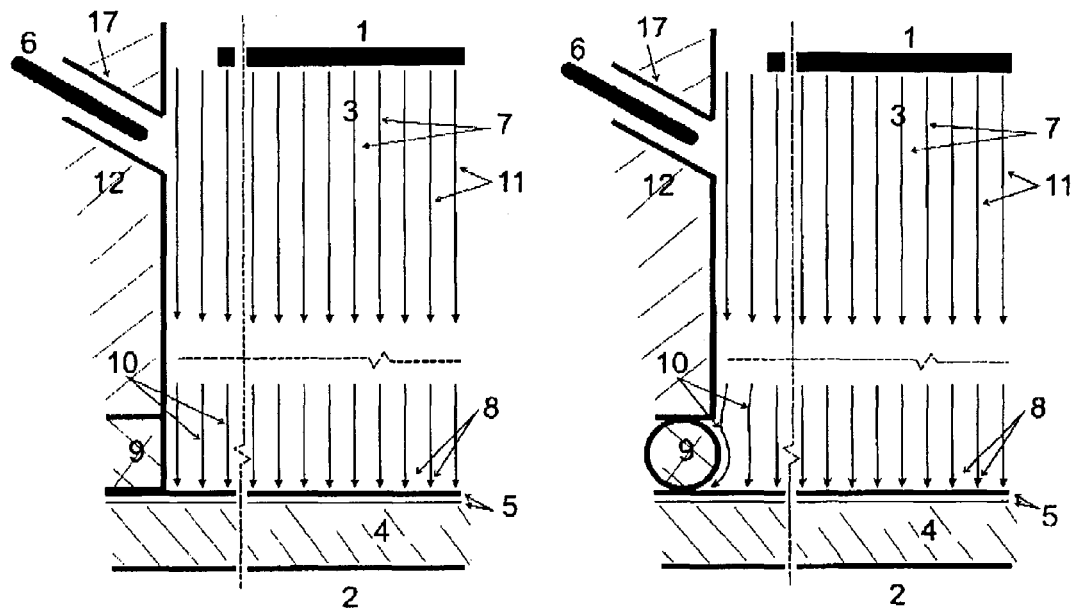
FIG. 9 schematically illustrates an electrochemical cell featuring a gasket that is rectilinear.
FIG. 10 schematically illustrates an electrochemical cell featuring a gasket that is circular in cross-section.
Figure 11:
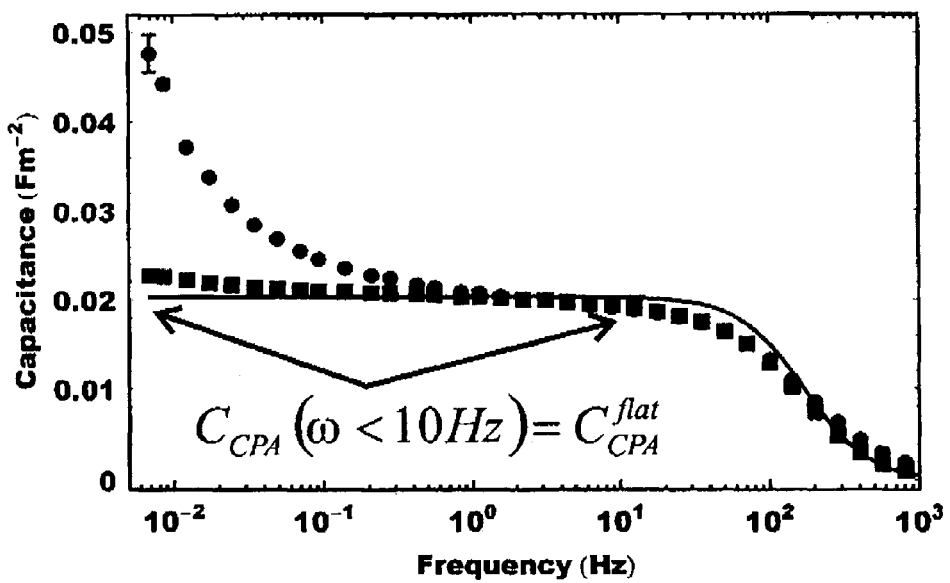
FIG. 11 graphically illustrates electrical impedance measurements of a 3 mM KCl solution at high frequencies using the apparatus of FIG. 9 (squares) and FIG. 10 (circles).

Effects of Non-Uniform Current Densities Produced by the Gasket on Measurements of Impedance FIGS. 9 and 10 schematically illustrate an electrochemical cell featuring a gasket that is either rectilinear (FIG. 9) or circular in cross-section (FIG. 10). Note that the reference electrode is retracted in the recess 17 of the top of the apparatus 12. FIG. 11 graphically illustrates two electrical impedance measurements of a 3 mM KCl solution in contact with a silicon wafer sample 5 at high frequencies in using the electrochemical cell shown in FIG. 9 (squares) and that shown in FIG. 10 (circles). The continuous curve is a plot of Equation (5) in which $m = -1$. At low frequencies this equation yields a capacitance for the CPA element that is independent of frequency.

FIG. 9 depicts a characterisation apparatus showing the preferred gasket of rectilinear cross-section located in line with the side wall 12 of the cell and the preferred location for the reference electrode 6 in the recess 17. The preferred location for the reference electrode averts disruption of the uniform current density that yields the differences in impedance and capacitance measurements of the rough gold surface shown in FIGS. 7 and 8.

The preferred gasket and its preferred location similarly avert disruption of the uniform current density 11 at the edges of the active area of the sample.

FIG. 11 compares area specific capacitance measurements of a solution in contact with an atomically flat silicon sample 4 and 5 using the two types of gaskets. Silicon readily oxidises forming a silicon dioxide surface 5 of comparable electrical and structural properties as the ionic double layer that forms at a metal-electrolyte interface.

Measurements made with either gasket approach similar capacitance values at high frequencies that are consistent with the negligibly small value expected for the electrolyte which is modelled by the resistive element R. Similarly, measurements made with either gasket converge to similar values at mid frequencies that are approximately independent of frequency, consistent with the trend expected for an atomically flat surface depicted in FIG. 11 as the continuous curve and consistent with the expected capacitance of a native silicon dioxide layer of thickness of 1.9 nm. Measurements made with the gasket of circular cross-section for frequencies decreasing further increasingly depart from those made using the gasket of rectilinear cross section and which largely retain the frequency independency expected for a flat surface and the capacitance value for a native silicon dioxide layer. The departure from the expected characterisation, which can only be attributed to the use of a gasket of circular cross section, represents an error in the characterisation through the use of a gasket that is not rectilinear in cross section.

The resolution of the characterisation of the sample and surface of small area in the apparatus is crucially dependent on maintaining the integrity of the whole surface 5 sealed by the gasket 9. The seal is formed and maintained by a pressure applied by the gasket on the surface 5 of the sample 4 supported firmly beneath by the working electrode 2 which is attached to the base 13. If the magnitude of the pressure is excessive then the topography of the surface under investigation can be compromised in the vicinity of the gasket. Further, if pressure is not uniform then excessive pressure can develop locally along the circumference of the gasket, potentially leading to a compromised tomography and even a perforated seal.

The proposed mechanism for controlling the magnitude and uniformity of the pressure relies on a set of springs 15A, 15B & 15C and supporting guide posts 14A, 14B & 14C. The spring constants and lengths of the springs are chosen such that the average pressures they can transmit to the sample 4 are insufficient to alter the tomography of the sample surface 5. FIG. 1 illustrates one means of controlling the pressure by threading bolts 16A, 16B and 16C onto the posts to the appropriate number of turns to achieve suitable spring tensions. The embodiment of FIG. 13 illustrates another arrangement for controlling the pressure by use of the threaded cap 18.

Although a single spring can control the average pressure on the sample it is difficult to devise a reliable physical means of converting the elastic force of the spring into a uniform pressure on the gasket and sample. This difficulty can be partially overcome by using two springs of the same tension located symmetrically on either the gasket. However, any misalignment or additional pressure applied to the top during assembly or when mounting electrodes, perfusion of the fluid, attaching perfusion tubing, etc., will result in a torque on the top of the apparatus that upon transmission to the gasket could compromise the tomography of the surface or perforate the seal. The addition of a third identical spring 15C at the same tension as the other two, opposes such torques ensuring that any additional applied pressure is transmitted more uniformly to the gasket. The use of additional springs will improve the uniformity further.

Electrochemical Characterisations of Samples and Surfaces

Experimental systems for characterising samples and surfaces are commonly based on apparatus that facilitate the injection of an electrical current through a sample of the layer (or surface) and enable the measurement and determination of the electric potential response of that sample to the current stimulus. The salient features for performing the characterisations in such an apparatus are depicted in FIG. 3 where electric current is represented by the black thin lines with arrows designating the direction of the current. The density of the direct current (dc) or alternating current (ac) can be inferred from the density of these lines.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A measurement cell in which a sample may be contained for electrochemical characterisation using three electrodes, the measurement cell comprising a sample container having a wall defining an interior region, an opening in a side wall of the container, an external passage extending outwardly from the opening and defining a space which is in fluid communication with the interior region of the sample container, a first, base electrode located an internal surface of a base of the sample container, a second, counter electrode located within the sample container and spaced from the first, base electrode by a distance in an axial direction of the sample container which greater than a spacing between the base electrode and the opening in the side wall of the sample container, and a third, reference electrode movably locatable in the space within the external passage.

2. The measurement cell as claimed in claim 1, wherein the sample comprises:
   a) a conductive liquid media contained in the container; or
   b) a sample element located over and in electrical contact with the base electrode or forming a surface of the base electrode and immersed in a conductive liquid media; and/or
   c) a sample element in contact with a conductive liquid media contained in the container, or
   d) a system combining two or more of a), b) and c), and wherein for each of a), b), c) & d) the conductive liquid media extends into the exterior passage and is of sufficient volume to contact the first, second, and third electrodes.

3. The measurement cell as claimed in claim 1, the container comprising a base such that the walls and the base define the interior region for containing the sample or a conductive liquid media with which the sample is in contact.

4. The measurement cell as claimed in claim 1 wherein the third, reference electrode is positionable with its distal end within the exterior passage such that in use the sample extends into the passage to contact the third, reference electrode with no part of the third, reference electrode extending into the interior region of the sample container.

5. The measurement cell as claimed in claim 1 wherein the container comprises a planar container base, and a tubular containment element defining the walls of an interior region of the container, a seal being provided between the tubular containment element and the container base, the first, base electrode forming an inner surface of the container base or in contact with the sample element which forms an inner surface of the container base and the inner surface of the container base extending to meet an inner surface of the tubular containment element, or an extension of the inner surface of the tubular containment element, the seal and the inner surface of the tubular containment element being arranged to form a uniform wall surface which extends to and intersects with the container base perpendicularly.

6. The measurement cell as claimed in claim 5 wherein the container base and the inner surface of the tubular containment element are smooth.

7. The measurement cell as claimed in claim 5 wherein the seal between the tubular containment element and the container base comprises a sealing element located between the container base and the tubular containment element, the sealing element having a rectilinear cross-section, an inner surface of the sealing element aligning with the inner surface of the side wall of the tubular containment element to form an extension of the inner surface of the tubular containment element.

8. The measurement cell as claimed in claim 7 wherein the tubular containment element is secured to the container base via a clamping device.

9. The measurement cell as claimed in claim 8 wherein spring elements are provided between the clamping device and the tubular containment element and the spring elements are provided with a spring constant corresponding to a design compression force of the sealing element whereby partial compression of the spring element applies sufficient compression of the sealing element to seal the tubular containment element to the container base without significantly distorting the inner surface of the sealing element such that it continues to be aligned as an extension of the inner surface of the tubular containment element.

10. The measurement cell as claimed in claim 8, wherein the clamping device includes a screw adjuster which provides adjustment of the pressure force clamping the elements together.

11. The measurement cell as claimed in claim 10 wherein the clamping device includes a single threaded screw element.

12. The measurement cell as claimed in claim 11 wherein the clamping device comprises a clamp base and one or more threaded rods secured to and extending perpendicularly from the base, the threaded rods extending through axially extending holes in the wall of the tubular containment element or extending adjacent the outside of the tubular containment element and nuts screw down on the threaded rods to bear on the tubular containment element to secure it in sealing engagement with the sealing element and the container base, by clamping the tubular containment element, the sealing element and the container base between the clamp base and the nuts.

13. The measurement cell as claimed in claim 12 wherein spring elements are provided between the nuts and respective bearing points on the tubular containment element, and the spring elements are provided with a spring constant corresponding to a design compression force of the sealing element whereby partial compression of the spring element applies sufficient compression of the sealing element to seal the tubular containment element to the container base without significantly distorting the inner surface of the sealing element such that it continues to be aligned as an extension of the inner surface of the tubular containment element.

14. A measurement cell in which a sample may be contained for electrochemical characterisation using three electrodes, the measurement cell comprising a sample container having a planar container base, and a tubular containment element defining the wall of an interior region in which the sample is contained, a seal being provided between the tubular containment element and the container base, the seal and the inner surface of the tubular containment element being arranged to form a uniform inner wall surface which extends to and intersects with the container base perpendicularly, an external passage in fluid communication with the interior region of the containment element via an opening in the wall of the inner region, a first, base electrode forming an inner surface of the container base and extending to meet the inner wall surface of the tubular containment element, a second, counter electrode located spaced from the first, base electrode in the sample container, and a third, reference electrode positionable within the external passage without extending into the interior region of the containment element to contact the sample between the first, base electrode and the second, counter electrode.

15. The measurement cell as claimed in claim 14, wherein the sample comprises:
  a) a conductive liquid media contained in the container; or
  b) a sample element located over and in electrical contact with the base electrode or forming a surface of the base electrode and immersed in a conductive liquid media; and/or
  c) a sample element in contact with a conductive liquid media contained in the container, or
  d) a system combining two or more of a), b) and c), and wherein in each of a), b), c), & d) the conductive liquid media extends into the exterior passage and is of sufficient volume to contact the first, second, and third electrodes.

16. A measurement cell in which a sample may be contained for electrochemical characterisation using three electrodes, the measurement cell comprising a container in which a sample is located, wherein the container has a planar container base, and a tubular containment element defining the walls of an interior region for containing a conductive media, a seal being provided between the tubular containment element and the container base, the seal and the inner surface of the tubular containment element being arranged to form a uniform inner wall surface which extends to and intersects with the container base perpendicularly, an external passage in fluid communication with the interior region of the containment element via an opening in the wall of the inner region, a first, base electrode forming an inner surface of the container base and the inner surface of the container base extending to meet the inner wall surface of the tubular containment element, a second, counter electrode located spaced from the first, base electrode in the container, and a third, reference electrode, which is positionable within the external passage without extending into the interior region of the containment element.

* * * * *

UNITED STATES PATENT AND TRADEMARK OFFICE
CERTIFICATE OF CORRECTION

PATENT NO.        : 8,512,535 B2
APPLICATION NO. : 12/675469
DATED             : August 20, 2013
INVENTOR(S)       : Coster et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 744 days.

Signed and Sealed this
Fifteenth Day of September, 2015

Michelle K. Lee
*Director of the United States Patent and Trademark Office*